United States Patent [19]
Richelsoph

[11] Patent Number: 5,628,747
[45] Date of Patent: May 13, 1997

[54] DEVICE FOR REMOVING CANCELLOUS BONE

[75] Inventor: Marc E. Richelsoph, Cordova, Tenn.

[73] Assignee: Wright medical Technology, Inc., Arlington, Tenn.

[21] Appl. No.: 7,702

[22] Filed: Jan. 22, 1993

[51] Int. Cl.[6] .................................................. A61F 2/30
[52] U.S. Cl. ............................................................ 606/79
[58] Field of Search ................................ 606/62, 79, 80, 606/84, 85, 86, 87, 88, 95, 96

[56] References Cited

U.S. PATENT DOCUMENTS

| | | | |
|---|---|---|---|
| 5,002,543 | 3/1991 | Bradshaw et al. | 606/62 |
| 5,156,602 | 10/1992 | Chin | 606/82 |

*Primary Examiner*—Angela D. Sykes
*Assistant Examiner*—Sonya Harris-Ogugua

[57] ABSTRACT

A device (10) for removing cancellous bone during machining of a long bone canal includes a brush mechanism for scraping cancellous bone from cortical bone while deflecting off the cortical bone and a center post (14) operatively connected to the brush mechanism (12) for centering the brush mechanism (12) relative to the long bone canal. An adapter mechanism (16) is connected to the center post (14) for connecting the center post (14) to a motion actuator to move the brush mechanism (12) relative to the long bone canal and scrape off cancellous bone therefrom.

16 Claims, 2 Drawing Sheets

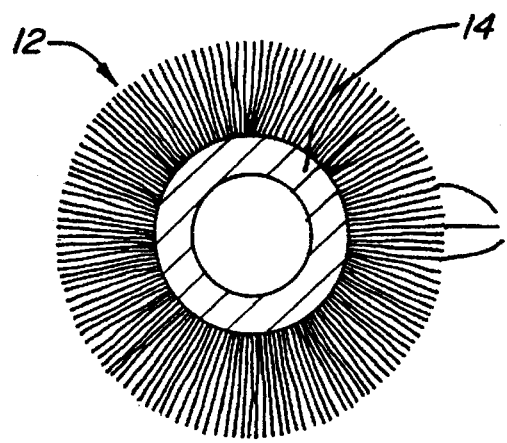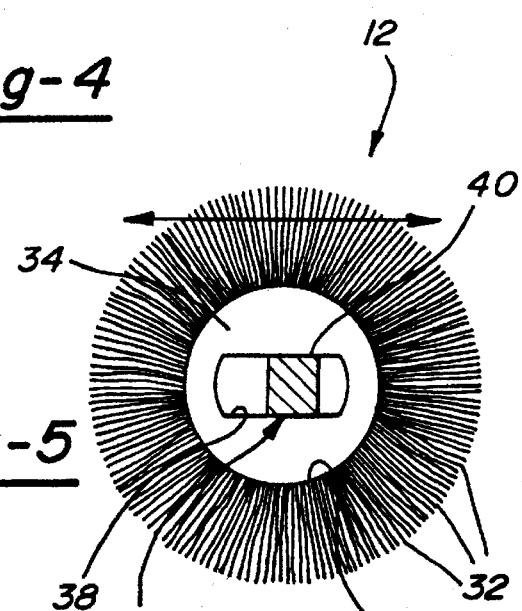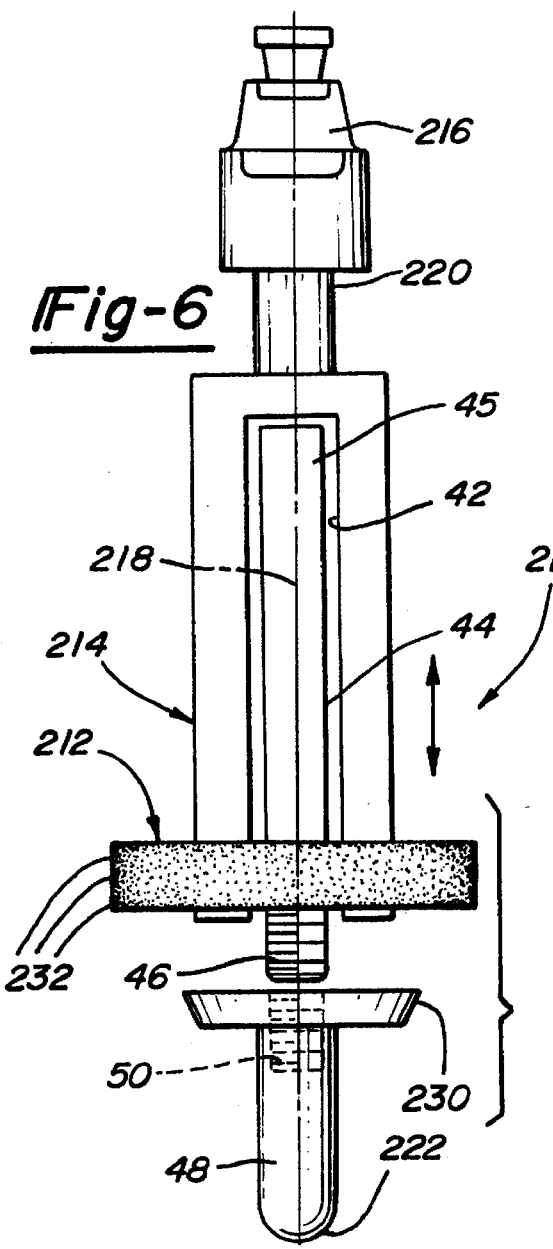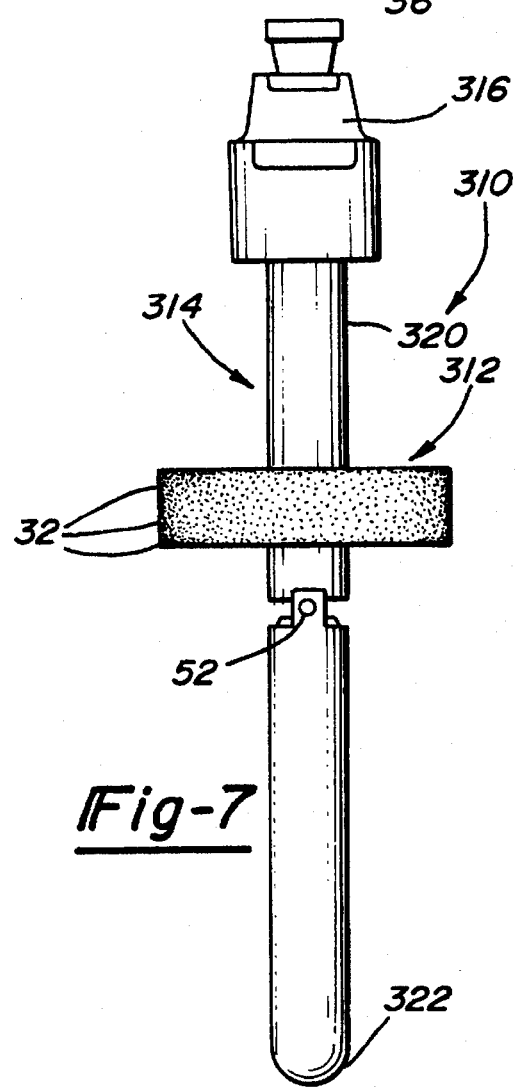

5,628,747

DEVICE FOR REMOVING CANCELLOUS BONE

TECHNICAL FIELD

The present invention relates to a device used during the preparation of a long bone, such as a femur, for the implantation of a prosthesis device. More specifically, the present invention provides a device for removing cancellous bone during the machining of a long bone canal, such as the femoral canal.

BACKGROUND OF THE INVENTION

During the preparation of the femur during standard cemented hip arthroplasty, the femoral canal is machined or broached to provide an oversized hole for the implant to rest in. This process is accomplished by hand-operated machining or broaching tools. After a bone plug is inserted and the canal cleaned by irrigation, cement is introduced into the canal and the hip stem is pushed into the cement and held in place until the cement mantel hardens. In order to achieve success during the process, the cement must reach and interdigitate with the hard cortical bone to guarantee good cement-bone interface strength. A difficulty arises when the cancellous bone is not sufficiently removed from the canal. Since the cancellous bone is weak, the cancellous bone provides an obstacle in achieving the interface strength. That is, although the cement may penetrate the cancellous bone, the cancellous bone does not provide a strong substrate for attachment to the prosthesis, thereby resulting in failure of the interface between the cement and bone.

Although the machining or broaching is done to remove cancellous bone and to prepare the cortical bone for hip stem implantation, the variations in bone shapes and sizes often require that the surgeon either leave the cancellous bone in place or remove it by curette and other hand techniques. These hand operated techniques are inaccurate, time consuming and rarely remove all of the cancellous bone. Therefore, it is desirable to have an instrument that will automatically remove the cancellous bone accurately and completely.

SUMMARY OF THE INVENTION

In accordance with the present invention, there is provided a device for removing cancellous bone during machining of a long bone canal, the device including brush means for scraping cancellous bone from the cortical bone while deflecting off of the cortical bone and guide means operatively connected to the brush means for centering the brush means relative to the long bone canal. Adapter means are connected to the guide means for connecting the guide means to a motion actuator to move the brush means relative to the lone bone canal and scrape cancellous bone therefrom.

FIGURES IN THE DRAWINGS

Other advantages of the present invention will be readily appreciated as the same becomes better understood by reference to the following Detailed Description when considered in connection with the accompanying Drawings wherein:

FIG. 4 is a cross-sectional view taken substantially along lines 4—4 of FIG. 1;

FIG. 5 is a cross-sectional view of an alternative embodiment of the invention showing the adapter wheel mounted on the center post;

FIG. 6 is a side view, partially in cross-section, of a third embodiment of the present invention; and FIG. 7 is an elongated side view of a fourth embodiment of the present invention.

DETAILED DESCRIPTION

Figure 1:
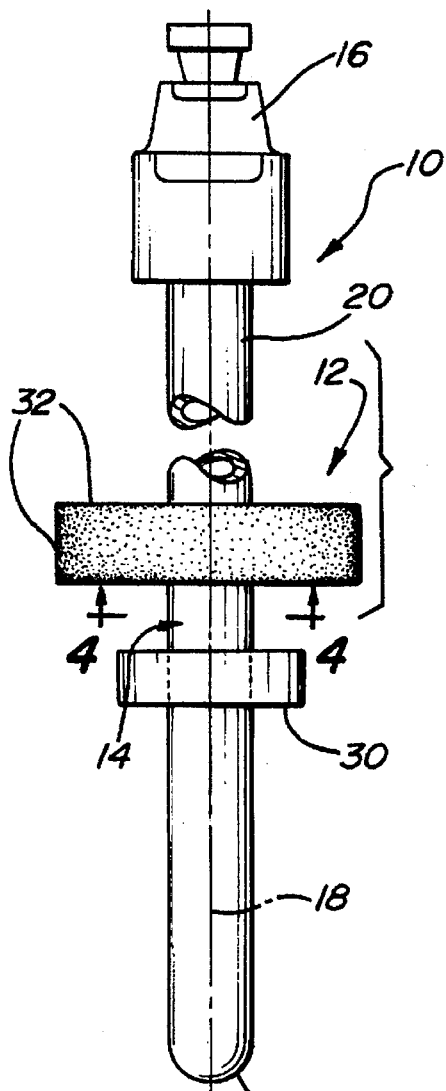
FIG. 1 is a side view of a device made in accordance with the present invention.

A device for removing cancellous bone during machining of a long bone canal is generally shown at 10 in the Figures. Like numerals preceded by the numerical suffix "1", "2" or "3" are used to show like structure between the several embodiments.

Generally, the device 10 includes a brush mechanism, generally shown at 12, for scraping cancellous bone from cortical bone while deflecting off of cortical bone. The brush mechanism 12 is operatively mounted upon a center post generally shown at 14. The center post provides a guiding mechanism for centering the brush mechanism 12 relative to the lone bone canal. An adapter mechanism, such as a Hutson reamer end 16, is connected to the center post 14 for connecting the center post 14 to a motion actuator to move the brush mechanism 12 relative to the long bone canal and scrape off cancellous bone therefrom. The Hutson reamer end 16 is an adapter well known in the art for connection to a reamer device for rotational movement of the center post 14. However, other adapters well known in the art, such as a bayonet, screw or other readily interchangeable adapter may be used with equal success. Such actuation can be for rotational movement of the center post 14 about its longitudinal axis (the axis defined by the length of the tool) indicated by broken line 18 in FIG. 1. The actuation can also be an axial reciprocating action along axis 18 as well.

In each embodiment of the invention, the center post 14 has a first and second end 20, 22, respectively. The adapter 16 is operatively connected to the first end 20, by means well known in the art. For example, the adapter 16 can be integrally mounted on the first end 20, the adapter 16 being an integral portion of the center post 14, or the adapter 16 can be removably mounted on the center post 20 for replacement to adapt the device to various types of reaming or piston actuated machining devices.

The second end 22 of the center post 14 is rod-shaped and has a rounded end surface for seating in the long bone canal. Thusly, the second end 22 of the device provides orientation of the center post 14 and thereby the brush mechanism 12 relative to the long bone canal during the operation of the device 10.

Figure 2:
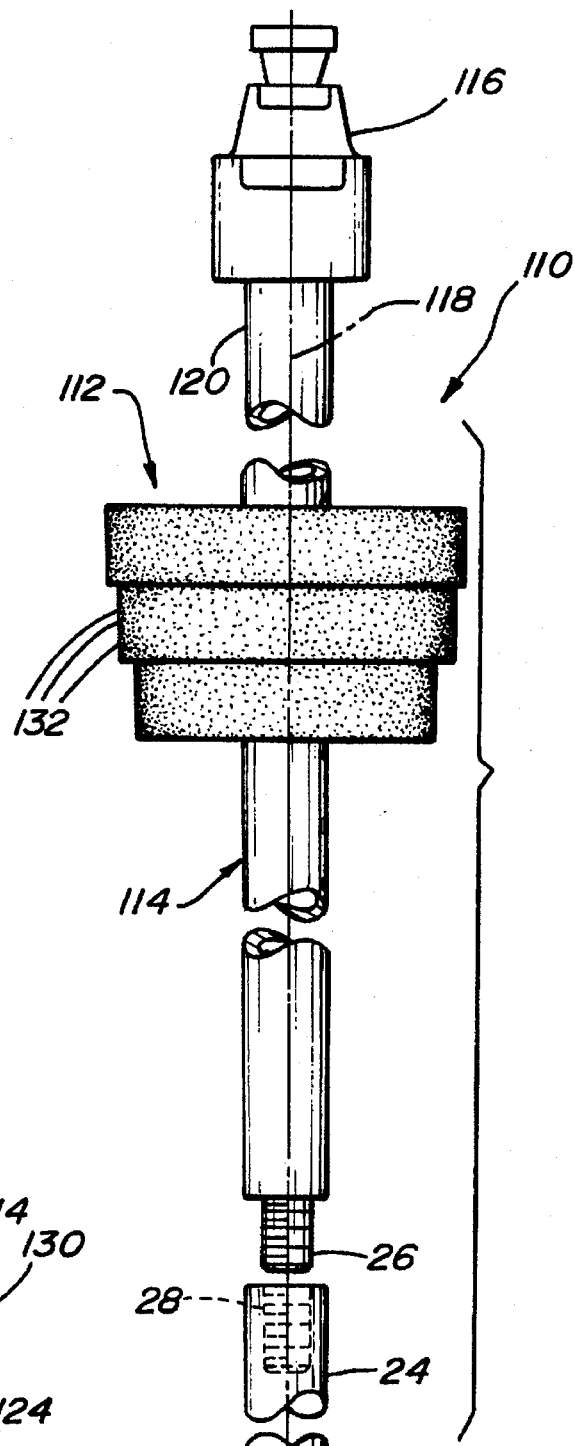
FIG. 2 is a side view of a second embodiment of the invention.
Figure 3:
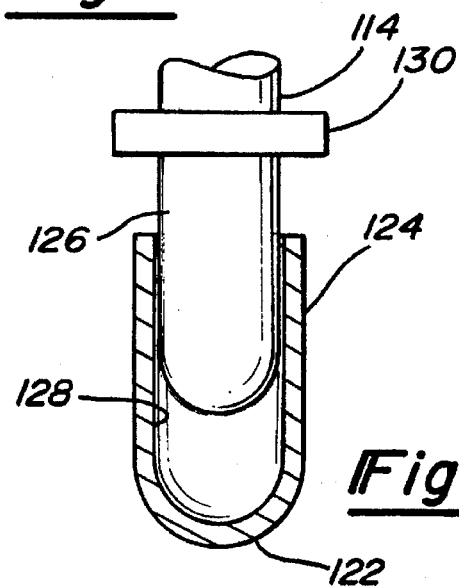
FIG. 3 is a fragmentary side view, partially in cross-section, of a sleeve member mounted on the center post of the device.

As shown in the several embodiments of FIGS. 1–3, the second end 22 of the center post 14 can include either an integral end portion, as shown in FIG. 1, or a sleeve 24 mounted on a sleeve mounting mechanism 26 defining an end of the center post 14. The sleeve member 24 can be constructed in various cross-sectional diameters allowing for sizing of the second end 22 of the center post 14 to various sized long bone canals.

For example, as shown in FIG. 2, the second end 122 of the center post 114 can include a sleeve member 24 having a threaded female portion 28 for engagement with the threaded male portion 26. Alternatively, the sleeve 24 could include a threaded male projection for engagement with a threaded female portion in the center post 114.

An alternative mounting mechanism is shown in FIG. 3. In this embodiment, the center post 114 includes a bayonet projection 126 which is seated in a recess 128. This embodiment allows for sliding movement of the bayonet projection 126 into and out of the recess 128 thereby allowing axial movement of the brush mechanism 112 relative to the long bone canal. Additionally, the cross-section of the recess 128 and projection 126 can be annular allowing for relative rotational movement between the bayonet projection 126 and recess 128. Alternatively, the bayonet projection can have a cross-sectional form which engages the recess 128 thereby requiring rotational movement of the sleeve 124 during actuated rotation of the center post 114.

The center post 14 can optionally include a stop mechanism extending radially therefrom for limiting the extent to which the center post 14 can enter the long bone canal. The stop mechanism can be in the form of an annular flange 30, 130, 230 shown in FIGS. 1, 3 and 6. The stop mechanism is operative by engaging the distal surface of the bone adjacent the canal thereof thereby limiting further insertion of the end portion 22 into the long bone canal. The annular flange 30 is disposed between the end portion 22 of the center post 14 and the brush mechanism 12.

The brush mechanism 12 can include a plurality of bristles 32 extending radially outwardly from the center post 14, as shown in cross-section in FIG. 4, and being disposed between the first and second ends 20, 22 of the center post 14, as shown in the Figures. More specifically, the bristles 32 can be connected directly to the center post 14 by means well known in the art, as shown in FIG. 4. For example, the wire bristles 32 can be attached by soldering or welding, or by crimping between two surfaces. Alternatively, if thicker and stiffer bristle 32 wires are desired, such bristles 32 may be pinned to the center post 14 to permit independent pivotal movement of each bristle 32 relative to the center post 14, not unlike the manner in which keys are retained on a standard key ring.

As shown in FIG. 4, the bristles 32 are mounted in an annular formation extending radially outwardly from the center post 14 thereby defining a wheel-type structure. The bristles can be made from wire, fibers, or other materials which can be constructed so as to be stiff enough to remove the cancellous bone yet deflect off of the cortical bone.

An alternative method of mounting the bristles 32 on the center post 14 is shown in FIG. 5. In this embodiment, the bristles 32 are mounted on an adapter wheel 34. The adapter wheel 34 includes an annular outer surface 36 upon which the bristles 32 are mounted by means well known in the art. The adapter wheel 34 includes a center slot opening 38 extending therethrough. The center post 14 includes a seating surface shown as a square-shaped surface 40, in cross-section, for seating the adapted member thereon whereby the flat surfaces of the opening 38 engage the flat surfaces of the seating surface 40 of the center post 14. The seating surface 40 of the center post 14 can be formed so as to substantially fill the opening 38 during mating thereof thereby allowing for no relative movement therebetween. Alternatively, as shown in FIG. 5, the seating surface 40 can allow for lateral i.e., side-to-side, movement of the adapter wheel 34 relative thereto thereby allowing for slight play between the adapter wheel 34 and center post 14. This allows the adapter wheel 34 movement to remove cancellous bone in a non-circular region of the canal. As the adapter wheel 34 turns at relatively low speeds, reaction forces applied to the adapter wheel 34 from cortical bone contact will force the adapter wheel 34 away, thus creating an ellipsoid for better cancellous bone removal.

The outer surface of the bristle 32 can be formed in various shapes which can be utilized for various canal configurations. More specifically, the bristles 32 are mounted along the length of the center post 14 as defined by the center axis 18 shown in FIG. 1. Preferably, as discussed above, the bristles 32 have ends radially distal from the center post 14. As shown in FIG. 1, these end portions can form a wheel-shape member 12 having a flat distal surface. As shown in FIG. 2, the assembly can include several wheel-shape members 112 each having a decreasing outer diameter in a step-wise manner. A further alternative embodiment, not shown in the Figures, would be a brush mechanism having a substantially frusto-conical shape, which is not step-wise as shown in FIG. 2. The configuration shown in FIG. 2 where the brushes 112 have step-wise decreasing outer surfaces, can be either formed by the bristles 132 being directly connected to the center post 114, as discussed above, or they can be separately mounted as individual wheels, also as discussed above with relation to the adapter wheel 34. By utilizing the adapter wheel 34, a single center post 14 can be used to either support a single wheel, as shown in FIG. 1, or multiple wheels as shown in FIG. 2, depending upon the situation encountered by the practitioner vis-à-vis the shape of the femoral canal being operated upon.

An alternative construction of the center post 214 of the present invention is shown in FIG. 6. The center post 214 includes a female portion 42 defining a guide track extending along a length of the center post 214 and a male portion 44 for seating in the female portion 42 while allowing for reciprocating axial motion relative therebetween. The reciprocating or piston-like motion provides axial reciprocating motion between the bristles 232 and the long bone canal. Thusly, similar to the embodiment shown in FIG. 3, the device 210 can provide combined rotational movement of the bristles 232 in addition to axial movement relative to the long axis 218 of the center post 214.

The device 210 shown in FIG. 6 can include a solid male portion 44 including a first end portion 45 for seating in the female portion 42 and a second end portion 222 as discussed above which is integral with the male portion 44. Alternatively, as shown in FIG. 6, the male portion 44 can include a second end 46 including threads thereon for connecting to a sleeve member 48. The sleeve member 48 includes a threaded female portion 50 for mounting on the threaded end portion 46, the sleeve member 48 providing a pilot stem proceeding within a long bone canal, as discussed above. The sleeve member 48 allows for sizing of the second end portion 122 of the male portion 44 to various sized long bone canals. That is, as discussed above, different sleeve members 48 having different cross-sectional diameters can be connected to a single male portion 44 thereby providing for adaptation of a single device to various sized and shaped long bone canals.

A further embodiment of the present invention is shown at 310 in FIG. 7. In this embodiment, the center post 314 includes a pivot mechanism 52 between the bristles 32 and the second end 322 of the center post 314 for allowing pivotal movement of the bristles 332 relative to the second end portion 322 and thereby relative to the long bone canal into which the second end 322 is seated. The pivot mechanism 52 can be in the form of a universal joint, ball joint, or the like, such joints being well known in the art. The pivot mechanism 52 allows a practitioner to move the bristles 32 in any direction desired relative to the femoral canal. Again, such a pivot mechanism 52 can be connected to a solid center post 14 by a sleeve member 48 including the pivot mechanism 52, as discussed above.

In operation, generally, an end portion 22 would be seated in the femoral canal. The center post 14, connected to a reamer device or the like by the adapter member 16, would be actuated to either rotate the center post 14 and attached bristles 32, to make the center post 14 move in piston-like manner, utilizing the device 210 shown in FIG. 6 or the bayonet sleeve connection shown in FIG. 3, or causing both a piston-like and rotational movement of the bristles 32. The operation would continue until the bristles 32 removed substantially all of the cancellous bone from the long bone canal. During the procedure, various end sleeve members, such as those shown in FIGS. 2 and 3 as well as a pivoting member 52, such as shown in FIG. 7, can be utilized. Thusly, the present invention provides an automatic device utilizing flexible wires or fibers attached to a center core, having varying dimensions depending on size requirements to remove cancellous bone during a standard cemented hip arthroplasty procedure.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A device (10) for removing cancellous bone during machining of a long bone canal, the device comprising:
   brush means (12) for scraping cancellous bone from cortical bone while deflecting off of cortical bone;
   guide means (14) operatively connected to the brush means (12) for centering the brush means (12) relative to the long bone canal; and
   adapter means (16) connected to the guide means (14) for connecting the guide means (14) to a motion actuator to move the brush means (12) relative to the long bone canal and scrape off cancellous bone therefrom.

2. A device (10) of claim 1 wherein the guide means (14) includes a center post (14) having a first and second end (20), (22), the adapter means (16) being operatively connected to the first end (20), the second end (22) being rod-shaped for seating in the long bone canal, and the brush means (12) including a plurality of bristles (32) extending radially outwardly from the center post (14) and being disposed between the first and second ends (20), (22).

3. A device (10) of claim 2 wherein the bristles (32) are connected directly to the center post (14).

4. A device (10) of claim 2 including an annular formation of the bristles (32) extending radially outwardly from the center post (14).

5. A device (10) of claim 2 wherein the bristles (32) are mounted along a length of the center post (14), the bristles (32) having ends radially distal from the center post (14) tapering radially inwardly towards the second end (46) of the center post (14) and defining a frusto-conical outer surface of the bristles (32).

6. A device (10) of claim 2 wherein the bristles (32) are mounted along a length of the center post (14) and define a wheel-shaped brush having an annular outer surface.

7. A device (10) of claim 2 including a plurality of wheel-shaped brushes (112) mounted adjacent each other along a length of the center post (14), each of the brushes having a different diameter thereby defining a step-wise tapering outer surface towards the second end (46) of the center post (14).

8. A device (10) for removing cancellous bone during machining of a long bone canal, the device comprising:
   brush means (12) for scraping cancellous bone from cortical bone while deflecting off of cortical bone;
   guide means (14) operatively connected to the brush means (12) for centering the brush means (12) relative to the long bone canal; the guide means (14) including a center post (14) having a first and second end (20), (22); and
   adapter means (16) connected to the guide means (14) for connecting the guide means (14) to a motion actuator to move the brush means (12) relative to the long bone canal and scrape off cancellous bone therefrom; the adapter means (16) being operatively connected to the first end (20) of the center post (14);
   the second end (22) of the center post (14) being rod-shaped for seating in the long bone canal;
   the brush means (12) including a plurality of bristles (32) extending radially outwardly from the center post (14) and being disposed between the first and second ends (20), (22);
   the second end (22) of the center post (14) including sleeve mounting means and a sleeve member (24) mounted thereon for seating within the long bone canal, the sleeve member (24) allowing for sizing of the second end (22) to various sized long bone canals.

9. A device (10) of claim 8 wherein the mounting means includes a threaded portion (30), the sleeve member (24) including a threaded portion (28) for mating engagement with the threaded portion (28) of the mounting means.

10. A device (10) of claim 9 wherein the mounting means includes a bayonet projection (126) and the sleeve member (124) includes a recess (128) for seating the bayonet projection (126) while allowing sliding movement of the bayonet projection (126) into and out of the recess (128) thereby allowing axial movement of the bristles (12) relative to the long bone canal.

11. A device (10) for removing cancellous bone during machining of a long bone canal, the device comprising:
   brush means (12) for scraping cancellous bone from cortical bone while deflecting off of cortical bone;
   guide means (14) operatively connected to the brush means (12) for centering the brush means (12) relative to the long bone canal; the guide means (14) including a center post (14) having a first and second end (20), (22); and
   adapter means (16) connected to the guide means (14) for connecting the guide means (14) to a motion actuator to move the brush means (12) relative to the long bone canal and scrape off cancellous bone therefrom; the adapter means (16) being operatively connected to the first end (20) of the center post (14);
   the second end (22) of the center post (14) being rod-shaped for seating in the long bone canal;
   the brush means (12) including a plurality of bristles (32) extending radially outwardly from the center post (14) and being disposed between the first and second ends (20), (22);
   the center post (14) including stop means extending radially therefrom for limiting how far the center post (14) can enter the long bone canal.

12. A device (10) of claim 11 wherein the stop means includes an annular flange (30) extending radially outwardly from the center post (14) between the bristles (12) and the second end (22) of the center post (14).

13. A device (210) for removing cancellous bone during machining of a long bone canal, the device comprising:

brush means (212) for scraping cancellous bone from cortical bone while deflecting off of cortical bone;

guide means (214) operatively connected to the brush means (212) for centering the brush means (212) relative to the long bone canal; the guide means (214) including a center post (214) having a first and second end (220), (222); and adapter means (216) connected to the guide means (214) for connecting the guide means (214) to a motion actuator to move the brush means (212) relative to the long bone canal and scrape off cancellous bone therefrom; the adapter means (216) being operatively connected to the first end (220) of the center post (214);

the second end (222) of the center post (214) being rod-shaped for seating in the long bone canal;

the brush means (212) including a plurality of bristles (232) extending radially outwardly from the center post (214) and being disposed between the first and second ends (220), (222);

the center post (214) including a female portion (42) defining a guide track extending along a length of the center post (214) and a male portion (44) for seating in the female portion (42) while allowing for reciprocating axial motion relative therebetween to provide axial reciprocating motion between the bristles (232) and the long bone canal.

14. A device (10) of claim 13 wherein the male portion (44) includes a first end (45) for seating in the female portion (42) and a second end (46) including mounting means for connecting a sleeve (48) thereto, the center post further including a sleeve member (48) mounted thereon for seating within the long bone canal, the sleeve member (48) allowing for sizing of the second end portion (122) of the male portion (44) to various sized long bone canals.

15. A device (10) for removing cancellous bone during machining of a long bone canal, the device comprising:

brush means (12) for scraping cancellous bone from cortical bone while deflecting off of cortical bone;

guide means (14) operatively connected to the brush means (12) for centering the brush means (12) relative to the long bone canal; the guide means (14) including a center post (14) having a first and second end (20), (22); and adapter means (16) connected to the guide means (14) for connecting the guide means (14) to a motion actuator to move the brush means (12) relative to the long bone canal and scrape off cancellous bone therefrom; the adapter means (16) being operatively connected to the first end (20) of the center post (14);

the second end (22) of the center post (14) being rod-shaped for seating in the long bone canal;

the brush means (12) including a plurality of bristles (32) extending radially outwardly from the center post (14) and being disposed between the first and second ends (20), (22); the bristles (32) are mounted on an adapter wheel (34) including an opening (38) extending therethrough, the center post (14) including a seating surface (40) for seating the adapter wheel (34) thereon.

16. A device (310) for removing cancellous bone during machining of a long bone canal, the device comprising:

brush means (312) for scraping cancellous bone from cortical bone while deflecting off of cortical bone;

guide means (314) operatively connected to the brush means (312) for centering the brush means (312) relative to the long bone canal; the guide means (314) including a center post (314) having a first and second end (320), (322); and adapter means (316) connected to the guide means (314) for connecting the guide means (314) to a motion actuator to move the brush means (312) relative to the long bone canal and scrape off cancellous bone therefrom; the adapter means (316) being operatively connected to the first end (320) of the center post (314);

the second end (322) of the center post (314) being rod-shaped for seating in the long bone canal;

the brush means (312) including a plurality of bristles (332) extending radially outwardly from the center post (314) and being disposed between the first and second ends (320), (322);

the center post (314) including a pivot means (52) between the bristles (332) and the second end (322) for allowing pivoting movement of the bristles (332) relative to the second end (322).

* * * * *